United States Patent [19]
Cook et al.

[11] Patent Number: 6,077,868
[45] Date of Patent: Jun. 20, 2000

[54] SELECTIVE INHIBITION OF CYCLOOXYGENASE-2

[75] Inventors: Mark E Cook; Leah D Whigham; Michael W Pariza, all of Madison, Wis.

[73] Assignee: Wisconsin Alumni Research Foundation, Madison, Wis.

[21] Appl. No.: 09/357,268

[22] Filed: Jul. 20, 1999

[51] Int. Cl.$^7$ .................................................. A61K 31/201
[52] U.S. Cl. .................................................. 514/560
[58] Field of Search .............................................. 514/560

[56] References Cited

U.S. PATENT DOCUMENTS

| | | | |
|---|---|---|---|
| 4,434,101 | 2/1984 | Cohen et al. | 260/410.9 R |
| 5,017,614 | 5/1991 | Pariza et al. | 514/558 |
| 5,070,104 | 12/1991 | Pariza et al. | 514/549 |
| 5,428,072 | 6/1995 | Cook et al. | 514/560 |
| 5,430,066 | 7/1995 | Cook et al. | 514/560 |
| 5,554,646 | 9/1996 | Cook et al. | 514/560 |
| 5,760,082 | 6/1998 | Cook et al. | 514/560 |
| 5,760,259 | 6/1998 | Gordon et al. | 554/224 |
| 5,851,572 | 12/1998 | Cook et al. | 426/2 |
| 5,914,346 | 6/1999 | Cook et al. | 514/558 |

OTHER PUBLICATIONS

Kim et al., Han'guk Sikp'um Yongyang Kwahak Hoechi, 26(5), 972–977 (abstract), 1997.

Cowley, Geoffrey "Getting a Grip on Pain," Newsweek (Dec. 14, 1998).

Hamberg, M., "Oxidation of Octadecatrienoic Acids in the red Alga Lithothamnion corallioides: Structural and Stereochemical Studies of Conjugated Tetraene Fatty Acids and Bis Allylic Hydroxy Acids," J. Chem. Soc, Perkin Trans. 1:3065–3072 (1993).

Hayek, et al., "Dietary Conjugated Linoleic Acid Influences the Immune Response of Young and Old C57BL/6NCrIBR Mice," J. Nutr. 129:32–38 (1999).

Li, et al., "Conjugated Linoleic Acids Alter Bone Fatty Acid Composition and Reduce ex vivo Prostaglandin E2 Biosynthesis in Rats Fed n–6 or n–3 Fatty Acids," Lipids 33:417–425 (1998).

Liu et al, "Conjugated linoleic acid reduces arachidonic acid content and PGE2 synthesis in murine keratinocytes," Cancer Letters 127:15–22 (1998).

Nugteren, I.H., "Inhibition of Prostaglandin Biosynthesis by 8CIS, 12TRANS, 14CIS–Eicosatetraenoic Acid," Chimica Et Biophysica Acta 210:171–176 (1970).

Proceedings, "The International Symposium Eicosanoids, Aspirin and Asthma," (Web Document, last updated Jul. 21, 1998).

Reilly, Joseph, "Nonsteroidal Anti–inflammatory Drugs: An Essential Class of Drugs Revisited," (Web Document, NY State Council of Health–System Pharmacists 1998).

Simmons et al., P.N.A.S. U.S.A. 86:1178–1182 (1989).

Sugano et al, "Lymphatic recovery, tissue distribution, and metabolic effects of conjugated linoleic acid in rats," J. Nutritional Biochem. 8:38–43 (1997).

Sugano et al., "Conjugated Linoleic Acid Modulates Tissue Levels of Chemical Mediators and Immunoglobulins in Rats," Lipids 33:521–527 (1998).

Williams, et al., "Prostaglandin endoperoxide synthase: Why two isoforms?" Am. J. Physiol. 270 (Gastrointest. Liver Physiol. 33):G393–G400 (1996).

Li, Y. et al., "Dietary Conjugated Linoleic Acids Alter Serum IGF–I and IGF Binding Protein Concentrations and Reduce Bone Formation in Rats Fed (n–6) 0r (n–3) Fatty Acids," *J. Bone Miner. Res.* 14:1153–1162 (1999).

*Primary Examiner*—Phyllis G. Spivack
*Attorney, Agent, or Firm*—Quarles & Brady LLP

[57] ABSTRACT

Disclosed is a method for selectively inhibiting cyclooxygenase-2 in an animal having a cyclooxygenase-2 activity by delivering into the animal an amount of a conjugated linoleic acid effective to reduce cyclooxygenase-2 activity in the animal.

7 Claims, 2 Drawing Sheets

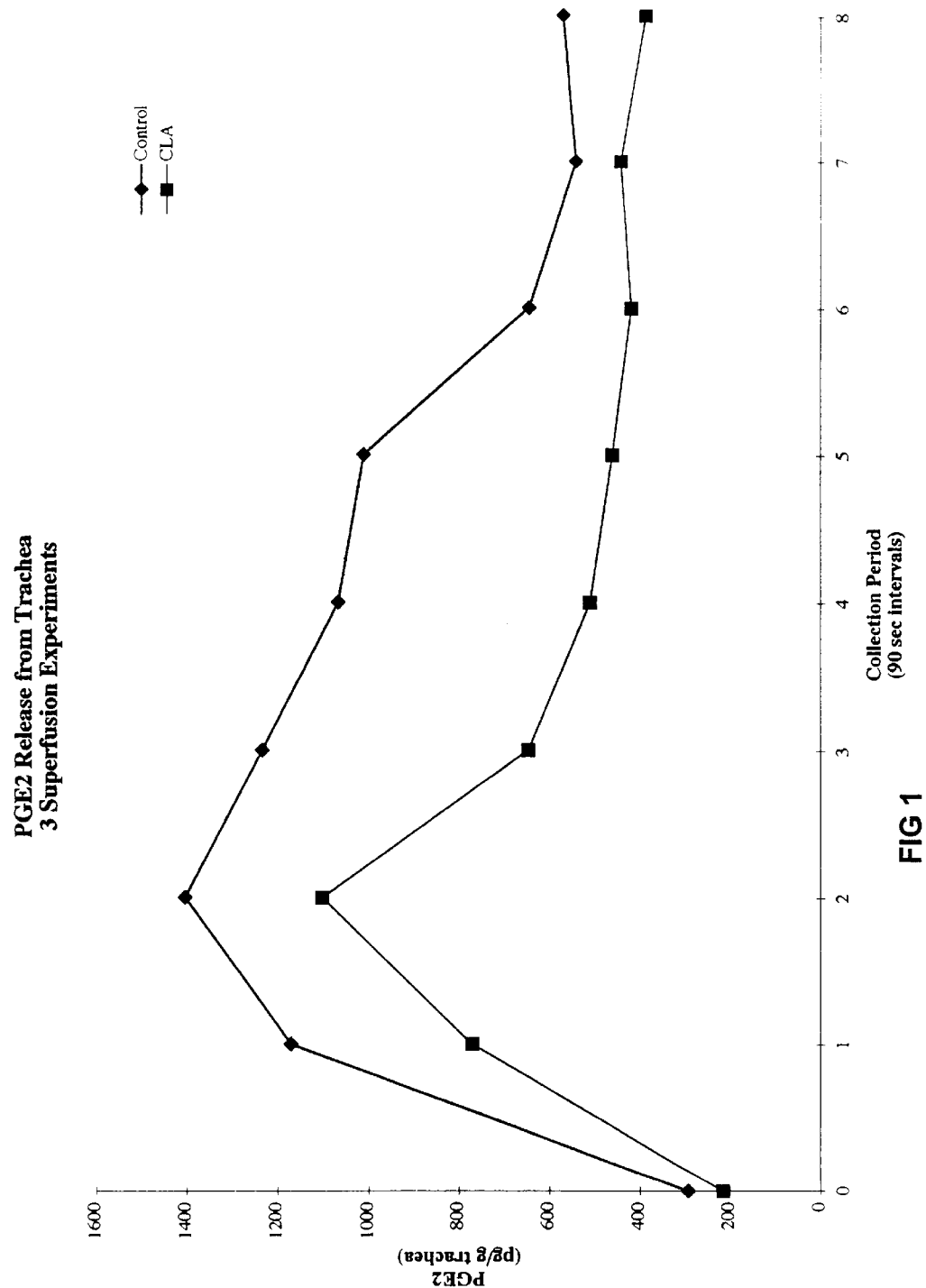

SELECTIVE INHIBITION OF CYCLOOXYGENASE-2

BACKGROUND OF THE INVENTION

Inflammatory reactions and associated pain can be induced by prostaglandins. Inflammation can be reduced by inhibiting prostaglandin biosynthesis. Most non-steroidal anti-inflammatory drugs (NSAIDs), including aspirin, inhibit prostaglandin synthesis by inhibiting cyclooxygenase, a key regulated enzyme in synthesis of 20 carbon eicosenoids, including prostaglandin E2 ($PGE_2$), from arachidonic acid. However, complete inhibition of prostaglandin synthesis is disfavored because prostaglandins also beneficially maintain the digestive tract lining. In the absence of prostaglandins, a propensity for ulcers and similar digestive problems can develop. This is particularly problematic for people suffering from conditions such as arthritis, the treatment of which generally requires long-term use of relatively large doses of anti-inflammatory agents.

The cyclooxygenase enzymes are reviewed by Williams, C. S. and R. N. DuBois, "Prostaglandin endoperoxide synthase: Why two isoforms?" *Am. J. Physiol.* 270 (Gastrointest. Liver Physiol. 33):G393–G400 (1996), incorporated herein by reference in its entirety. Briefly, cyclooxygenase exists in at least two different enzyme isoforms (Simmons et al., P.N.A.S. U.S.A. 86:1178–1182 (1989)), designated-Cox-1 and Cox-2. Cox-1 is involved in synthesizing housekeeping prostaglandins that function to maintain the digestive tract lining. In contrast, Cox-2 catalyzes the synthesis of prostaglandins that cause inflammation and pain, but does not appear to catalyze housekeeping prostaglandins. Both Cox-1 and Cox-2 are involved in producing precursors for several prostanoids including $PGE_2$.

Cox-1 is expressed constitutively at relatively stable levels in many tissues, whereas Cox-2 expression can be induced by a variety of chemicals, including, but not limited to, lipopolysaccharides, phorbal esters, interleukin-1, tumor necrosis factor, human chorionic gonadotropin, and platelet activating factor. As a result of this distinction, one can characterize the relative contribution of each isoform to the overall $PGE_2$ level by comparing basal $PGE_2$ levels to the levels after induction.

Because existing drugs that bind both Cox-1 and Cox-2 can cause significant undesired gastric side effects, considerable attention has been directed toward developing pain relief medications that specifically inhibit Cox-2 enzyme activity without affecting Cox-1 enzyme activity. Recently, the Food and Drug Administration approved one such medication, Celebrex, only for the treatment of arthritis pain, pending further studies. Preliminary results suggest that Celebrex provides pain relief and reduces inflammation without causing stomach problems. Unfortunately, Celebrex is expensive.

Accordingly, there is currently a strong interest in developing pharmaceuticals and therapies that reduce inflammation and provide pain relief without causing associated stomach problems.

Conjugated linoleic acid reduces liver and serum $PGE_2$ levels in rats fed a diet containing 1% CLA (Sugano, et al. *Nutritional Biochem.* 8:38–43, 1997). Liu et al. (Cancer Lett. 127:15–22, 1998) suggested that CLA inhibits $PGE_2$ synthesis by cyclooxygenase by competing with the enzyme's substrate, arachidonic acid. It was not known whether conjugated linoleic acids inhibit both Cox-1 and Cox-2.

BRIEF SUMMARY OF THE INVENTION

The present invention is a method of selectively inhibiting Cox-2 in an animal expressing Cox-2, the method comprising the step of administering to the animal a conjugated linoleic acid in an amount effective to selectively reduce the activity of Cox-2 without substantially reducing the activity of Cox-1. Selective reduction of Cox-2 activity can be assessed by comparing levels of $PGE_2$ before and after inducing Cox-2 expression, as described herein.

It is an object of the present invention to selectively reduce the activity of Cox-2 enzyme without substantially reducing the activity of Cox-1.

It is an advantage of the present invention that conjugated linoleic acid is generally regarded as safe and non-toxic when administered to animals and humans.

It is another advantage of the present invention that conjugated linoleic acid can be obtained and used without prescription.

BRIEF DESCRIPTION OF THE SEVERAL VIEWS OF THE DRAWINGS

FIG. 1 shows the magnitude and time course of prostaglandin $E_2$ ($PGE_2$)release from superfused trachea of sensitized guinea pigs fed a control diet (diamonds) or a diet containing 0.25% CLA (squares) before (collection period 0) and after (periods 1–8) antigen challenge.

DETAILED DESCRIPTION OF THE INVENTION

Figure 2A:
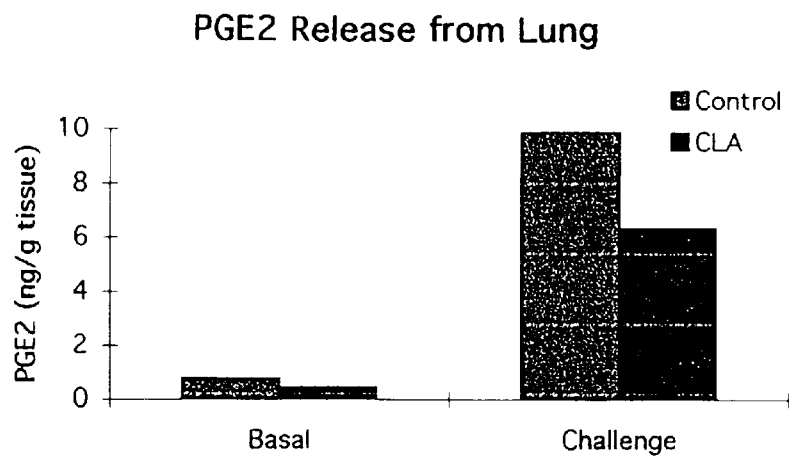
FIGS. 2A–2C shows the release of $PGE_2$ from lung (A), bladder (B), and trachea (C) tissue from sensitized guinea pigs with or without (basal) antigen challenge.

The inventors have recognized, and disclose herein, that conjugated linoleic acid (CLA) selectively inhibits Cox-2 enzyme activity without significantly reducing Cox-1 enzyme activity in animals administered an amount of CLA effective to inhibit Cox-2 enzyme activity. This observation was not previously noted, and permits advantageous therapeutic interventions that satisfy a stated object of the present invention. The observation is important because the housekeeping functions of Cox-1 are maintained without adverse effect, while the inflammatory response and pain associated with Cox-2-directed prostaglandin synthesis can be controlled.

Accordingly, one aspect of the present invention is a method for selectively inhibiting cyclooxygenase 2 (Cox-2) in an animal expressing Cox-2, the method comprising the step of administering to the animal an amount of at least one conjugated linoleic acid isomer effective to selectively reduce the activity of Cox-2 without substantially affecting cyclooxygenase 1 (Cox-1) activity. The absolute percent reduction of Cox-2 activity is less critical than the in vivo effects caused by reduced Cox-2 activity. What is important is that CLA inhibits Cox-2 activity to an extent sufficient to reduce inflammation, without causing stomach problems.

The effect is most readily studied in an ex vivo model system, although by carefully selecting an appropriate model system, namely guinea pigs, one can reasonably predict success in mammals, including humans and domesticated animals such as farm animals and pets. In the model system, Cox-2 activity is preferably reduced by at least about 10% in tissue from animals fed a diet containing CLA. More preferably, Cox-2 activity is reduced by 20% or even 50% or more. At the same time, Cox-1 activity is reduced insignificantly.

The effect of CLA on cyclooxygenase activity can also be expressed as the percentage ratio of the Cox-2:Cox-1 reduction. Preferably, the percentage ratio is maximized so as to afford effective pain relief and reduced inflammation, without interfering with the maintenance functions of Cox-1. Preferably, this ratio is at least about 2:1. More preferably, this ratio is at least about 20:1, or even about 50:1.

In this application "conjugated linoleic acid" or "CLA" means an unsaturated fatty acid having 18 carbons and two conjugated double bonds, the fatty acid being selected from the group consisting of 18:2(9c,11t), 18:2(9t,11c), 18:2(10c,12t) and 18:2 (10t,12c), and also including bioactive esters and salts thereof, and mixtures thereof. The CLA may be administered by any convenient means. Preferably, the conjugated linoleic acid is delivered orally in a capsule, tablet, or chewable form comprising conjugated linoleic acid and a pharmaceutically acceptable ingestible carrier. It is envisioned that the CLA can be administered orally for timed-release delivery. Alternatively, the CLA may be formulated for intravenous, intramuscular, transdermal, or transmucosal administration. Since CLA is generally regarded as safe, the precise amount of CLA administered is not considered critical, as long as it is sufficient to achieve a stated object of the invention. For example, if fed to an animal, an appropriate amount of CLA in the diet is in the range of 0.1% to 5% by weight, preferably 0.2% to 0.5% by weight in the diet. If administered by another route, CLA can be effectively administered at a dosage ranging from about 1 mg/kg to about 1000 mg/kg body weight of the animal or higher. This corresponds to about 0.1 g/day to about 40 g/day for a person weighing 45 kg.

In the following non-limiting examples, Cox-1 and Cox-2 activity were measured indirectly by monitoring the levels of $PGE_2$ released from excised tissue of sensitized animals fed CLA or CLA-free diets, in the presence or absence of an inducing antigenic challenge. The examples demonstrate that the method of the present invention is effective in reducing Cox-2 directed $PGE_2$ production in guinea pigs, a preferred model system for evaluating immune and inflammatory responses in mammals, including humans. Since the chemical structure of COX-2 substrates are the same in all animal species, it is reasonably predicted from these trials that the method of the present invention will achieve selective inhibition of Cox-2 in any animal having the Cox-2 isoform, including in humans.

$PGE_2$ levels were measured in excised tissue from guinea pigs fed (or not fed) CLA and sensitized to an antigen using tracheal superfusion or tissue baths containing lung, bladder, or tracheal tissue. One wishing to monitor Cox-2 response to CLA could alternatively measure the amount of Cox-2 protein or Cox-2 mRNA formed in appropriate tissues.

In the absence of an inducing antigen challenge, tissue from CLA-fed animals exhibits only slight decreases in $PGE_2$ production, relative to animals fed a CLA-free control diet. In contrast, in tissue subjected to inducing antigen challenge, much greater $PGE_2$ reduction was observed in tissue from animals fed CLA in the diet than in tissue from animals fed CLA-free diets. These results suggest that the CLA specifically inhibits the inducible Cox-2 enzyme activity to a much greater extent than it inhibits the constitutively expressed Cox-1 enzyme activity.

The invention will be better understood upon consideration of the following non-limiting examples.

EXAMPLE 1

Superfusion

Diets and Sensitization

Three experiments were completed using identical conditions in each of the three experiments, except where otherwise noted. Female Hartley guinea pigs (Harlan, Madison, Wis.) weighing 200–350 g were housed in a temperature- and humidity-controlled room with a 12 hour light-dark cycle. The guinea pigs were randomly divided into two diet groups (n=6 guinea pigs/treatment in experiments 1 and 3, n=3 guinea pigs/treatment in experiment 2). One of the two groups received a control diet which comprised a standard guinea pig diet (Harlan-Teklad) supplemented with 0.25% corn oil (experiment 1) or 0.25% linoleic acid (Nu-Check prep; experiments 2 and 3). The second set of animals in each experiment received a standard guinea pig diet (Harlan-Teklad) supplemented with 0.25% conjugated linoleic acid (CLA) synthesized from linoleic acid by previously described methods (Chin, et al., J. Food Comp. and Anal. 5:185–197 (1992)).

The guinea pigs were given free access to the experimental diets for at least 1 week prior to and during active sensitization to chicken egg ovalbumin (OVA, Sigma) antigen. Guinea pigs were sensitized with an initial intraperitoneal (IP) injection of 50 ug OVA in PBS with aluminum hydroxide followed two weeks later by a subcutaneous injection (flank) of 200 ug OVA in PBS emulsified with equal volume of Incomplete Freund's Adjuvant. The animals were sacrificed 4 days after the second injection of OVA by an intraperitoneal injection of sodium pentobarbital.

Tracheal Superfusion

The tracheas of the sensitized guinea pigs were removed shortly after the animals were killed and transferred to petri dishes containing a bicarbonate buffered physiological saline solution (PSS)(118 mM NaCl, 1.0 mM $NaH_2PO_4$, 4.7 mM KCl, 2.5 mM $CaCl_2$, 0.5 mM $MgCl_2$, 11 mM glucose, and 25 mM $NaHCO_3$). Excess tissue was removed from the tracheas, taking care to avoid stretching or abrading the tracheas. Each trachea was cut longitudinally at a 45° angle into a spiral (Constantine, 1965) and suspended in an air-filled, water-jacketed tissue chamber maintained at 37° C. The tracheas were superfused at a rate of 2.2 ml/min with PSS (37° C., gassed with 95% $O_2$ and 5% $CO_2$) while being kept at a tension of 5 g for an equilibration period of 90 minutes. Changes in tensions were measured with FT 03 electrical force transducers and plotted with a Grass polygraph. Following equilibration, tracheas were challenged by continuously superfusing PSS containing 0.01 mg/ml OVA. Superfusates were continually collected in 90 sec intervals beginning 90 sec before antigen challenge (designated collection period 0) and placed at 4° C. Peak changes in tracheal tensions were determined for each 90 sec collection period. Superfusates were analyzed for histamine and $PGE_2$ content. Following antigen challenge, tracheas were continuously superfused with PSS containing $10^{-5}$ carbachol (carbamylcholine chloride, Sigma) to produce a maximum contractile response. Following carbachol contractions, tracheas were weighed, minced with scissors and homogenized in 0.4 N percholoric acid, and placed in a boiling water bath for 10 min for to extract residual histamine.

Mediator Analysis

The $PGE_2$ content of superfusates was determined using the room temperature protocol of an enzyme immunoassay system (Amersham Life Science). The sensitivity of this assay is 40 pg/ml. Cross reactivity with $PGE_1$, $PGF_{2\alpha}$, 6-keto-$PGF_{1\alpha}$, and arachidonic acid is 25%, 0.04%, <0.1%, and <0.001%, respectively.

Results

FIG. 1 shows the amount of $PGE_2$ released from tracheas of CLA-fed and CLA-free animals before and after induction of Cox-2 activity. Before induction (collection period 0), the CLA-fed and CLA-free animals both produce low levels of $PGE_2$, although CLA-fed animals produce slightly less $PGE_2$ than CLA-free animals, possibly reflecting an inhibition of endogenous low level Cox-2 activity. After induction (collection periods 1–8), CLA-fed animals consistently produce less $PGE_2$ than CLA-free animals, thereby demonstrating that an increase in $PGE_2$ synthesis attributable to induction of Cox-2 can be substantially reduced by administering CLA that inhibits Cox-2 activity.

EXAMPLE 2

Tissue Bath Data

Diets and Sensitization

The diet and sensitization protocols for two tissues bath experiments were essentially as described above for the superfusion experiments, with n=3 guinea pigs/treatment in experiment 1 and n=6 guinea pigs/treatment in experiment 2. The control diets contained 0.25% safflower oil, and CLA-90 (Natural) was used for CLA diets.

Tissue Bath Experiments

Following sensitization and sacrifice as described above, the lungs, trachea, and bladder were removed from the guinea pigs. Each tissue was weighed, placed in 37° C. PSS baths, and allowed to equilibrate in the baths for at least one hour. The OVA antigen was added to the baths, and after one hour baths were collected for analysis of $PGE_2$ and $LTB_4$ release. Basal levels of release were determined from bath buffer collected prior to antigen challenge.

Mediator Analysis

The $PGE_2$ and $LTB_4$ contents of tissue bath samples were analyzed using enzyme immunoassay systems (Amersham Life Science). The $PGE_2$ assay was as described above. The sensitivity of the $LTB_4$ assay is 6 pg/ml, and the cross-reactivities with 20-OH-$LTB_4$, 6-trans-$LTB_4$, $LTC_4$, $LTD_4$, 5-hydroxyeicosatetraenoic acid (5-HETE), and 12-HETE are 2.0, 25.5, 0.011, 0.010, 0.008, and 0.034, respectively.

Results

Figure 2B:
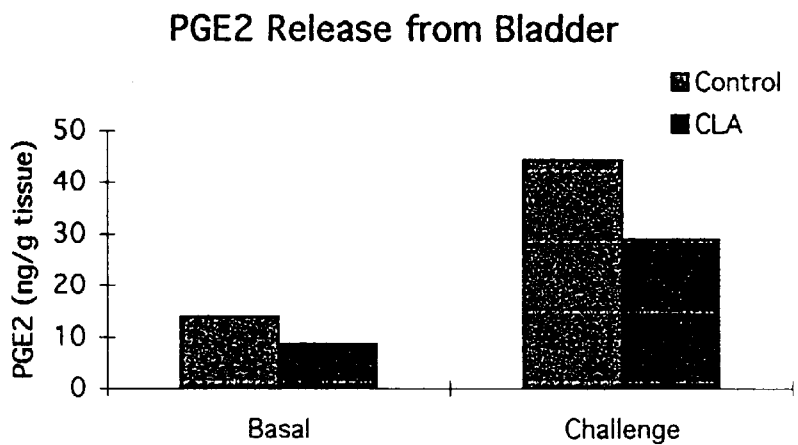
Figure 2C:
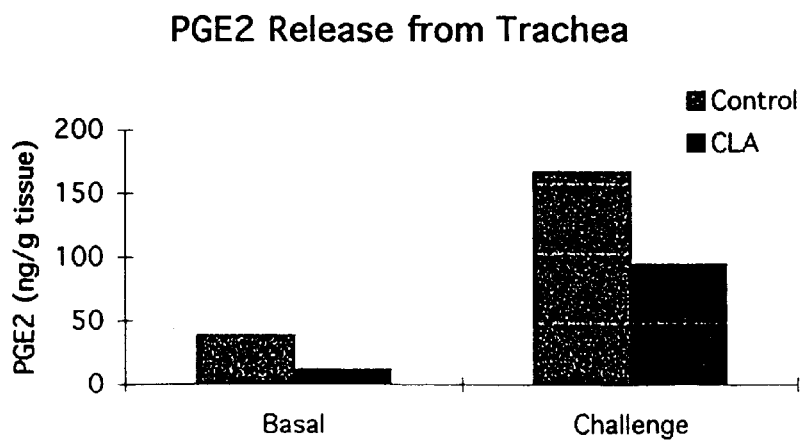

FIGS. 2A–2C shows the amount of $PGE_2$ released from lung (FIG. 2A), bladder (FIG. 2B) and trachea (FIG. 2C) of CLA-fed and CLA-free animals before and after induction of Cox-2 activity. Before induction (basal level), the CLA-fed and CLA-free animals both produce low levels of $PGE_2$, although CLA-fed animals produce slightly less $PGE_2$ than CLA-free animals, possibly reflecting an inhibition of endogenous low level Cox-2 activity. After induction (challenge level), CLA-fed animals consistently produce less $PGE_2$ than CLA-free animals, thereby demonstrating that an increase in $PGE_2$ synthesis attributable to induction of Cox-2 can be substantially reduced by administering CLA that inhibits Cox-2 activity.

All publications cited in the specification are incorporated by reference.

The present invention is not limited to the exemplified embodiments, but is intended to encompass all such modifications and variations as come within the scope of the following claims.

We claim:

1. A method for selectively inhibiting cyclooxygenase 2 activity in an animal having cyclooxygenase 2 activity, comprising the step of:

administering to the animal an amount of a conjugated linoleic acid (CLA) effective to reduce the activity of cyclooxygenase 2.

2. The method of claim 1, wherein the administering step comprises a method selected from the group consisting of oral delivery, intramuscular injection, intravenous injection, transdermal delivery, and transmucosal delivery.

3. The method of claim 1, wherein the administering step comprises oral delivery.

4. The method of claim 1, wherein the animal is a human.

5. The method of claim 1, wherein the conjugated linoleic acid is selected from the group consisting of an 18:2(9c,11t) isomer, an 18:2(9t,11c) isomer, an 18:2(10c,12t) isomer, an 18:2 (10t,12c) isomer, a bioactive ester thereof, a salt thereof, and a mixture thereof.

6. The method of claim 1, wherein the CLA is delivered in a dosage of between about 1 mg/kg and 1000 mg/kg body weight of the animal.

7. A method for reducing cyclooxvyenase 2-mediated inflammation in an animal comprising the step of delivering into the animal an amount of a conjugated linoleic acid effective to reduce the inflammation without causing gastric irritation.

* * * * *